United States Patent [19]

Benjamin et al.

[11] Patent Number: 4,837,239
[45] Date of Patent: Jun. 6, 1989

[54] CARDIOTONIC PHOSPHODIESTERASE INHIBITORS COMPLEXED WITH WATER SOLUBLE VITAMINS

[75] Inventors: Eric J. Benjamin, Dublin, Ohio; Gary C. Visor, Half Moon Bay, Calif.

[73] Assignee: Syntex (U.S.A.) Inc., Palo Alto, Calif.

[21] Appl. No.: 918,449

[22] Filed: Oct. 14, 1986

Related U.S. Application Data

[63] Continuation-in-part of Ser. No. 768,549, Aug. 23, 1985, abandoned.

[51] Int. Cl.$^4$ .................. A61K 31/505; A61K 31/51; A61K 31/525; C07D 487/04
[52] U.S. Cl. ............................. 514/267; 514/233.2; 544/115; 544/250
[58] Field of Search ............... 514/267, 234, 236, 230; 544/250, 115

[56] References Cited

U.S. PATENT DOCUMENTS

| | | | |
|---|---|---|---|
| Re. 31,617 | 6/1984 | Beverung, Jr. et al. | 544/250 |
| 3,128,227 | 4/1964 | Kanegis et al. | 514/153 |
| 3,282,778 | 11/1966 | Lobel | 514/161 |
| 3,932,407 | 1/1976 | Beverung, Jr. et al. | 544/250 |
| 3,983,119 | 9/1976 | Beverung, Jr. et al. | 544/250 |
| 3,983,120 | 9/1976 | Beverung, Jr. et al. | 544/250 |
| 3,988,340 | 10/1976 | Partyka et al. | 544/250 |
| 4,092,410 | 5/1978 | Ogata et al. | 424/78 |
| 4,146,718 | 3/1979 | Jenks et al. | 544/292 |
| 4,208,521 | 6/1980 | Crenshaw et al. | 544/250 |
| 4,256,748 | 3/1981 | Chodnekar et al. | 514/267 |
| 4,357,330 | 11/1982 | Fleming, Jr. et al. | 514/267 X |
| 4,390,540 | 6/1983 | Chodnekar et al. | 514/267 |
| 4,432,980 | 2/1984 | Fleming, Jr. et al. | 514/267 |
| 4,444,777 | 4/1984 | Fleming, Jr. et al. | 514/267 |
| 4,490,371 | 12/1984 | Jones et al. | 514/267 X |
| 4,551,459 | 11/1985 | Jones et al. | 514/267 |
| 4,568,676 | 2/1986 | Smith | 514/258 |
| 4,591,592 | 5/1986 | Chowhan | 514/301 |
| 4,593,029 | 6/1986 | Venuti et al. | 514/267 |
| 4,596,806 | 6/1986 | Ishikawa et al. | 514/267 |
| 4,610,987 | 9/1986 | Ishikawa | 514/239 |
| 4,663,320 | 5/1987 | Jones et al. | 514/212 |
| 4,670,434 | 6/1987 | Venuti | 514/234 |
| 4,690,925 | 9/1987 | Fried et al. | 514/267 |

FOREIGN PATENT DOCUMENTS

| | | | |
|---|---|---|---|
| 45238 | 2/1982 | European Pat. Off. | |
| 0116948 | 8/1984 | European Pat. Off. | 544/250 |
| 0153152 | 8/1985 | European Pat. Off. | 514/267 |
| 1450960 | 9/1976 | United Kingdom | |
| 2001638 | 2/1979 | United Kingdom | |

OTHER PUBLICATIONS

The Merck Index, 8th Ed., Stecher, Ed., Merck & Co., Rahway, N.J., (1968), p. 178.

Remington's Pharmaceutical Sciences, 16th Ed., Osol. Ed., Mack Co., (1980), pp. 1483-1484.

Chien, "Solubilization of Metronidazole by Water-Miscible Multi-Cosolvents and Water-Soluble Vitamins", *J. of Parenteral Science and Technology*, 38(1), 32,36 (1984).

Higuchi and Bolton, "The Solubility and Complexing Properties of Oxytetracycline and Tetracycline III", *J. Amer. Pharmaceutical Assoc.*, 48(10), 557-564 (1959).

Truelove et al., "Solubility Enhancement of Some Developmental Anti-Cancer Mucleoside Analogs by Complex Action With Nicotinamide", *Intern. J. of Pharmaceutics*, 19, 17-25 (1984).

(List continued on next page.)

Primary Examiner—Donald G. Daus
Assistant Examiner—Diana G. Rivers
Attorney, Agent, or Firm—Liza K. Toth; Brian Lewis; Tom M. Moran

[57] ABSTRACT

This invention is directed to a formulation of cardiotonic phosphodiesterase inhibitors with a water-soluble vitamin, comprising a lyophilization step performed on a solution of the complex in an aqueous/organic solvent system. The formulation results in a complex that has been found to have enhanced solubility (over the compound alone) in a parenterally or orally acceptable solvent, and the lyophilization process yields a product with superior stability permitting an extended shelf life.

24 Claims, 6 Drawing Sheets

OTHER PUBLICATIONS

Fawzi et al., "Rationalization of Drug Complexation in Aqueous Solution by Use of Huckel Frontier Mulecular Orbitals", *J. Pharm. Sci.*, 69, 104–106 (1980).

Derwent #37757A Corresponding to J7 8012568 to Takeda Chemical Ind. KK. (1978).

Derwent #37796A Corresponding to RD 169009 to Anonymous.

Derwent #83-767946 Corresponding to J5 8135822 to Chugai Pharmaceutical KK.

Derwent #86-216099 Corresponding to J6 1148123 to Daiichi Seiyaku KK.

Derwent #66850T to Alkaloida Vegyeszeti Gyar.

Derwent #32880C to Groning, R.

Derwent #80059D to Merck & Co. Inc.

Derwent #21320F to Takeda Chem Ind. Ltd.

Derwent #85-239345 to Hisamitsu.

M of Complexing Agents

N-cyclohexyl-N-methyl-4-(2-oxo-1,2,3,5-tetrahydroimidazo[2,1-b]
quinazolin-7-yl)oxybutyramide Hydrogen Sulfate solubility
dependence on complexing agent concentration as determined
by phase-solubility experiments with Ascorbic Acid (●),
Pyridoxine (O), Thiamine (▲), and Nicotinamide (△).
All determinations were made at 25°C pH 2.0

A comparison of solubility enhancement obtained for compound as the result of solution phase complexation (△) and following freeze drying 50:50 aqueous:tert-butyl alcohol mixtures (◇)

CARDIOTONIC PHOSPHODIESTERASE INHIBITORS COMPLEXED WITH WATER SOLUBLE VITAMINS

Related Application

This is a continuation-in-part of U.S. patent application Ser. No. 768,549, filed Aug. 23, 1985, now abandoned, and assigned to the assignee of the present invention.

BACKGROUND OF THE INVENTION

1. Field of the Invention

This invention generally relates to formulations and methods of formulating cardiotonic phosphodiesterase (PDE) inhibitors. Of particular interest are those compounds which are (2-oxo-1,2,3,5-tetrahydroimidazo[2,1-b]quinazolinyl)oxyalkylamides.

2. Related Art

Exemplary compounds of this general class are known in the prior art. In particular, U.S. Pat. No. 4,490,371 and its continuation U.S. Pat. No. 4,551,459 disclose a series of (2-oxo-1,2,3,5-tetrahydroimidazo[2,1-b]quinazolinyl)-oxyalkylamides as cyclic AMP phosphodiesterase inhibitors useful as antithrombotic agents and the like in mammals, and also having inotropic and anti-metastatic activities. The U.S. Pat. No. 4,490,371, as well as U.S. Pat. No. 4,551,459 (issuing from Ser. No. 599,858), and U.S. Pat. No. 4,663,320, (issuing from Ser. No. 744,100), assigned to the assignee of the present invention, are hereby fully incorporated into this patent application by reference.

In general, phosphodiesterase inhibitors are known to have limited solubility and stability in water. In particular, it has been found that with the (2-oxo-1,2,3,5-tetrahydroimidazo-[2,1-b]-quinazolinyl)-oxalylamides of U.S. Pat. Nos. 4,490,371 and 4,551,459, cosolvent systems of varying compositions (e.g., in the range of 10 to 50% ethanol, polyethylene glycol or the like) improve the solubility only slightly, and increase the incidence of local irritation in parenteral administration. In order to most conveniently administer the disclosed compounds intravenously, a need exists to develop a formulation that will enhance their solubility in water, while providing sufficient stability to maintain a commercially acceptable shelf life of at least two years.

SUMMARY OF THE INVENTION

According to a first aspect of the invention, a lyophylized complex is disclosed comprising:

a water-soluble vitamin or a pharmaceutically acceptable salt thereof; and a cardiotonic phosphodiesterase inhibitor, an optical isomer thereof, or a pharmaceutically acceptable acid addition salt thereof, preferably, a (2-oxo-1,2,3,5-tetrahydroimidazo-[2,1-b]quinazolinyl) oxyalkylamide compound of the formula

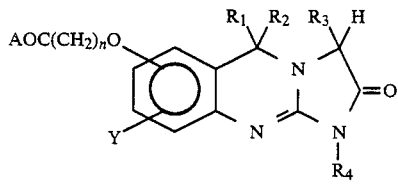

(I)

wherein n is an integer of 1 to 6;

$R_1$ is hydrogen or alkyl of 1 to 4 carbons;

$R_2$ is hydrogen or $R_1$ and $R_2$ are combined to form an oxo group;

$R_3$ is hydrogen, alkyl of 1 to 6 carbons, phenyl, benzyl, hydroxy lower alkyl or an aliphatic acylate thereof of 1 to 6 carbon atoms or an aryl acylate thereof of 7 to 12 carbon atoms, carbamoyl alkyl, carboxyalkyl, alkoxycarbonylalkyl or an α-amino acid side chain;

$R_4$ is hydrogen, alkyl of 1 to 6 carbons, benzyl, or hydroxy lower alkyl;

Y is hydrogen, alkyl of 1 to 4 carbon atoms, halo or lower alkoxy;

A is $NR_5R_6$ wherein $R_5$ and $R_6$ are independently selected from the group consisting of: hydrogen; alkyl of 1 to 6 carbon atoms; hydroxyalkyl of 1 to 6 carbon atoms or an aliphatic acylate thereof of 1 to 6 carbon atoms or an aryl acylate thereof of 7 to 12 carbon atoms; cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_7$, halo, —NH$_2$, —N(R$_7$)$_2$, —NHCOR$_7$, —COOH, or —COO(R$_7$) group wherein $R_7$ is lower alkyl; phenyl or phenyl lower alkyl wherein phenyl is unsubstituted or substituted with at least one lower alkyl, halo or lower alkoxy group or an —NH$_2$, —N(R$_7$)$_2$, —NHCOR$_7$, —COOH, or —COOR$_7$ group wherein $R_7$ is lower alkyl; or wherein $R_5$ and $R_6$ are combined to form a compound selected from the group consisting of: morpholinyl; piperidinyl; perhexylenyl; N-loweralkylpiperazinyl; pyrolidinyl; tetrahydroquinolinyl; tetrahydroisoquinolinyl; (±)-decahydroquinolinyl and indolinyl.

These compounds of Formula (I) are described in U.S. Pat. Nos. 4,490,371 and 4,551,459.

According to a second aspect of the invention, an injectable formulation containing a lyophilized complex of a water-soluble vitamin or a pharmaceutically acceptable salt thereof and a therapeutically effective amount of a cardiotonic PDE inhibitor or a pharmaceutically acceptable salt thereof is disclosed.

According to a third aspect of the invention, a method is disclosed for formulating a lyophilized complex of a water-soluble vitamin or a pharmaceutically acceptable salt thereof, and a cardiotonic PDE inhibitor, or a pharmaceutically acceptable salt thereof, from an aqueous/organic solvent system in a lyophilization process.

An important object of the invention is to enhance the water solubility of the above-identified class of oxyalkylamides by complexation with water-soluble vitamins, followed by lyophilization from an aqueous/organic solvent system, preferably using a lower chain alcohol as a cosolvent.

Another object of the invention is to provide a formulation for said class of compounds that can be easily reconstituted for use in intravenous therapy and the like.

Yet another object of the invention is to provide a formulation that will have sufficient stability to endure a shelf life of at least two years.

Further objects and addendant advantages of this invention will be best understood by reference to the following detailed description, examples and drawings.

DETAILED DESCRIPTION OF THE PREFERRED EMBODIMENTS OF THE INVENTION

The formulations and methods for formulating cardiotonic PDE inhibitors, such as (2-oxo-1,2,3,5-tetrahydroimidazo-[2,1-b]quinazolinyl)oxyalkylamides, in accordance with the present invention relate to the complexation of these compounds with water-soluble vitamins followed by a lyophilization process. The formulations have improved solubility (over the oxyalkylamides alone) in a parenterally or orally acceptable solvent, such as water, propylene glycol, ethanol or polyethylene glycol. The preferred methods of formulating include a lyophilizaton step using a lower chain alcohol as a cosolvent, preferably ethanol, isopropanol, tert-butyl alcohol or n-propanol and yield a product having even greater water solubility as well as superior stability permitting an extended shelf life.

The limited solubility of phosphodiesterase inhibitors, in particular, the above-described class of oxyalkylamides (the compounds of Formula (I), for example of N-cyclohexyl-N-methyl-4-(2-oxo-1,2,3,5-tetrahydroimidazo-[2,1-b]quinazolin-7-yl)oxybutyramide and its pharmaceutically acceptable salts) results in a slow dissolution rate and in relatively poor bioavailability upon oral administration. To overcome these obstacles, "charge transfer" complexation with water-soluble vitamins (cofactors) was investigated by the present inventors.

Figure 1:
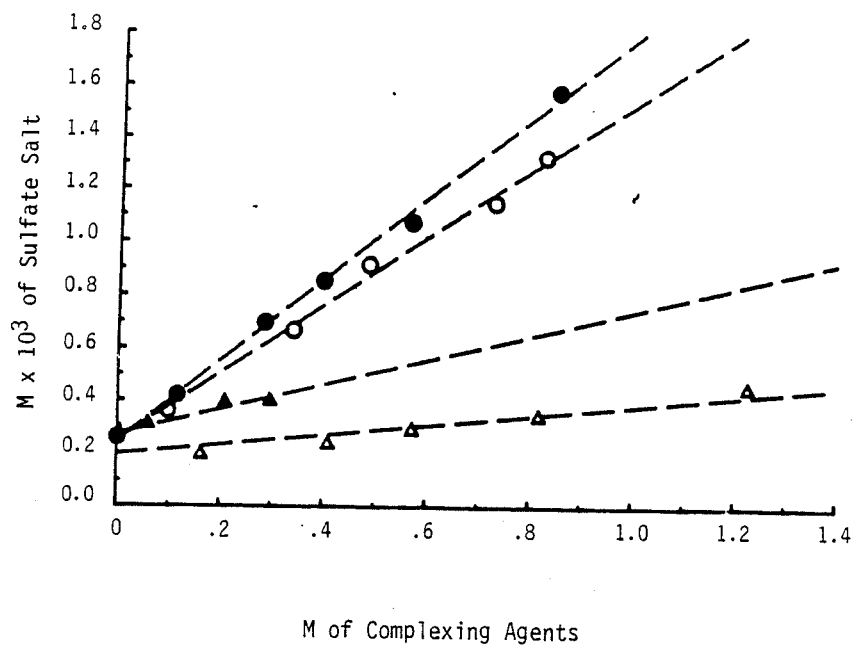
FIG. 1 is a graph demonstrating improved water solubility of N-cyclohexyl-N-methyl-4-(2-oxo-1,2,3,5-tetrahydroimidazo-[2,1-b]quinazolin-7-yl)oxybutyramide in the presence of water-soluble vitamins.
Figure 2:
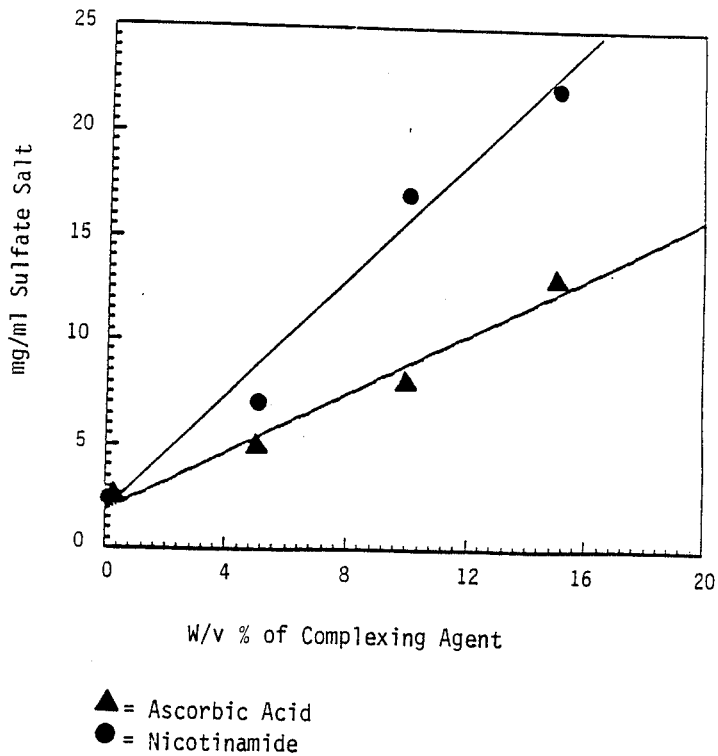
FIG. 2 is a graph showing improved water solubility of N-cyclohexyl-N-methyl-4-(2-oxo-1,2,3,5-tetrahydroimidazo-[2,1-b]quinazolin-7-yl)oxybutyramide in the presence of water soluble vitamins, and ethanol and propylene glycol.
Figure 4A:
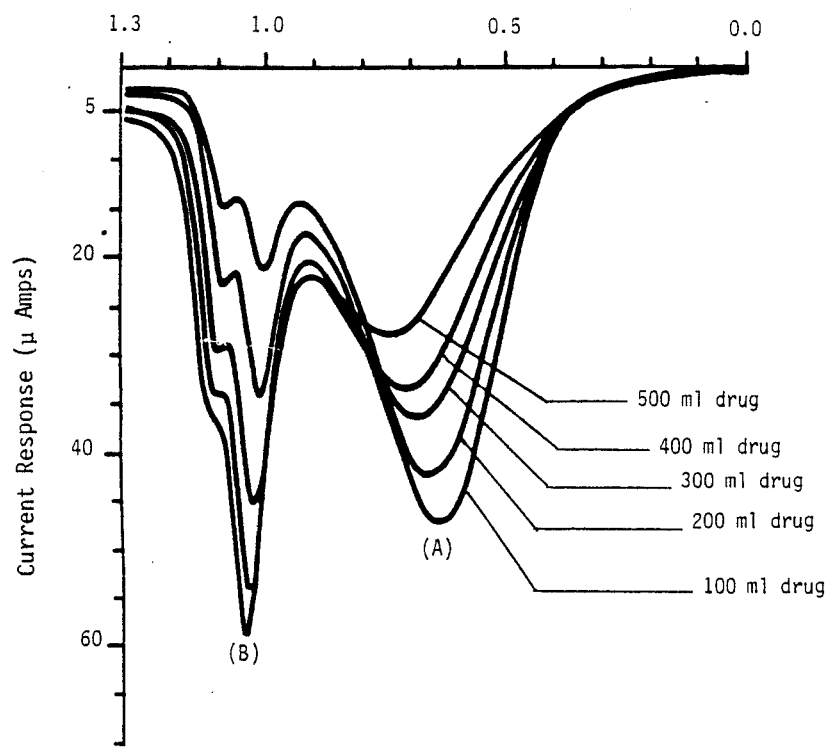
FIGS. 4a and 4b demonstrate the electrochemical interaction between ascorbic acid and N-cyclohexyl-N-methyl-4-(2-oxo-1,2,3,5-tetrahydroimidazo[2,1-b]quinazolin-7-yl)oxybutyramide in solution.
Figure 4B:
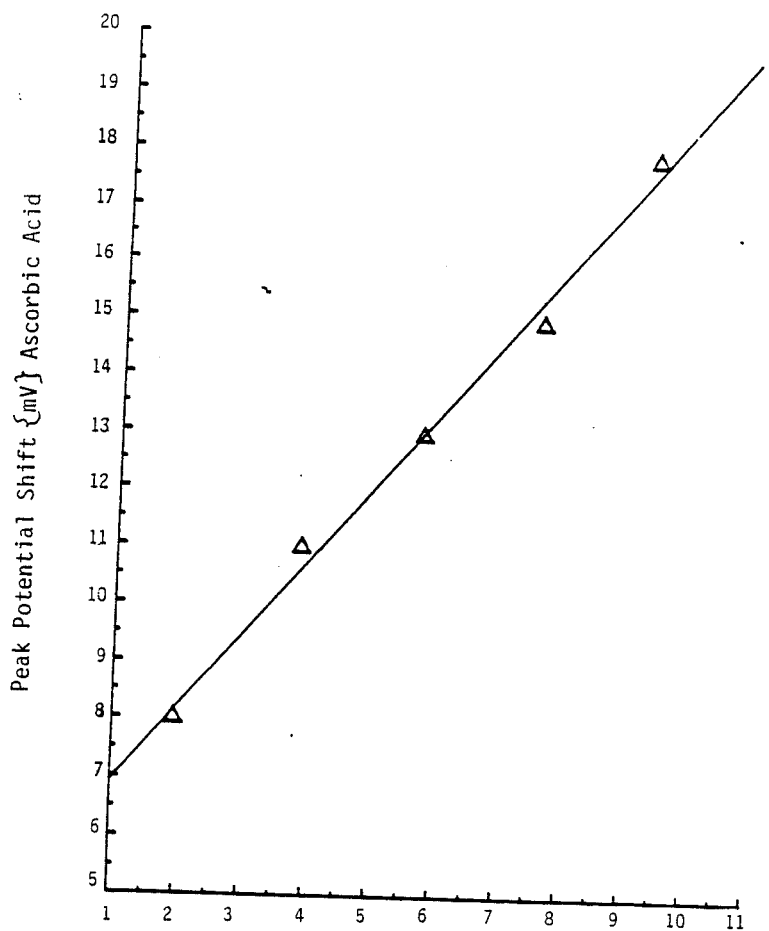

The present inventors have discovered that the compounds of Formula (I) form water-soluble complexes with water-soluble vitamins such as ascorbic acid, nicotinamide thiamine and pyridoxine. The phenomenon of complex formation can be confirmed by phase solubility experiments (FIGS. 1 and 2), and by spectral shifts and changes in electrochemical responses of the vitamins in the presence of these compounds (FIGS. 4a and 4b). For example, FIGS. 4a and 4b show the results of a titration of excess ascorbic acid with the hydrogen sulfate salt of N-cyclohexyl-N-methyl-4-(2-oxo-1,2,3,5-tetrahydroimidazo-[2,1-b]quinazolin-7-yl)oxybutyramide. It is hypothesized that the relatively planar tricyclic structure of the compound and the presence of non-bonding electrons on ring heteroatoms renders the compound capable of charge donation to suitable acceptors. In addition, the compound may also function as a charge acceptor due to the presence of a formal positive charge on a ring nitrogen at low pH (i.e., due to the presence of the planar cyclic cationic portion of the compound). Thus, the interaction with the water-soluble vitamin may be defined in terms of the existence of a charge transfer complex, resulting in enhanced water-solubility. FIGS. 4a and 4b support this hypothesis by showing a shift in the peak potential and a reduction of the peak current of ascorbic acid as the compound is added to the solution. This result is consistent with the more bulky species (i.e., the complex) requiring more energy in order to undergo oxidation at the electrode surface. The decrease in current is due to a lower diffusion coefficient of the complex.

Figure 5:
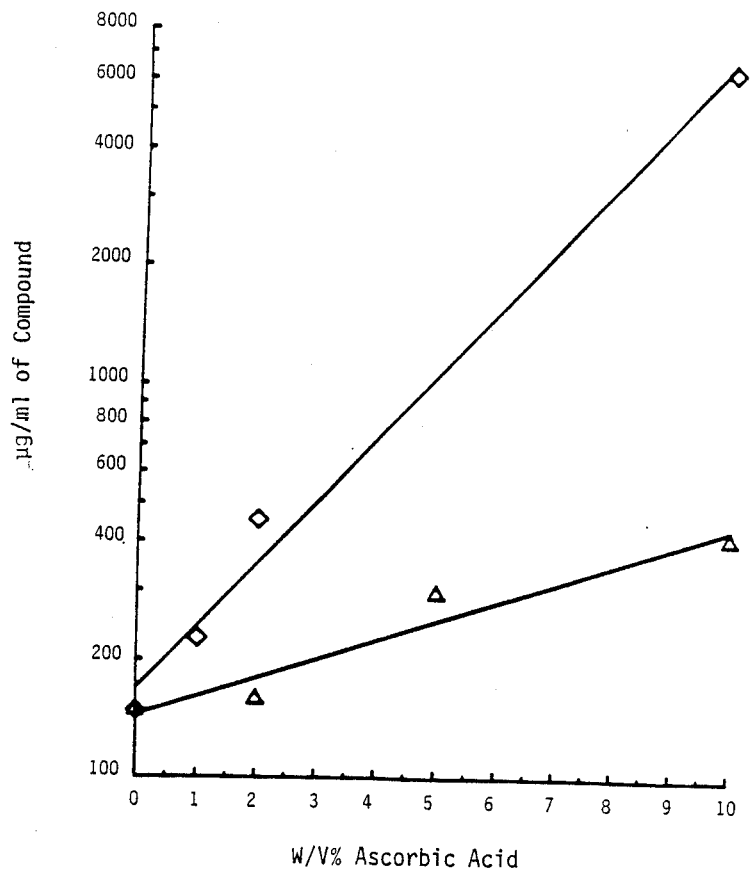
FIG. 5 is a graph showing the enhancement of solubility of N-cyclohexyl-N-methyl-4-(2-oxo-1,2,3,5-tetrahydroimidazo-[2,1-b]quinazolin-7-yl)oxybutyramide in complexation with a water soluble vitamin and lyophilization.

The phenomenon of complex formation significantly increases water solubility of the complex as compared with the water solubility of the drug alone. The improvement in solubility in the presence of water-soluble vitamins is specifically illustrated by FIGS. 1 and 2. For example, N-cyclohexyl-N-methyl-4-(2-oxo-1,2,3,5-tetrahydroimidazo-[2,1-b]quinazolin-7-yl)oxybutyramide (measured as the free base equivalent of the compound) is water-soluble only to the extent of about 120 $\mu$g/ml (about $0.2 \times 10^{-3}$M) at pH2 in the absence of water-soluble vitamin; in the presence of 10% (about 0.6M) ascorbic acid; however, the solubility is about 420 $\mu$g/ml (about $0.8 \times 10^{-3}$M) at pH2. The solubility is still further enhanced by the lyophilization process of the present invention. For example, if the lyophilization procedure described below is followed, N-cyclohexyl-N-methyl-4-(2-oxo-1,2,3,5-tetrahydroimidazo-[2,1-b]quinazolin-7-yl)oxybutyramide is water-soluble to the extent of about 5,000 $\mu$g/ml at pH2 using 10% ascorbic acid (See FIG. 5).

The water-soluble vitamins are especially attractive as complexing agents because of their high safety and low toxicity upon oral and parenteral administration. The soluble complexes disclosed herein will not only enable the formulation of an injectable solution, but will also enhance the oral absorption of the drugs due to a faster rate of dissolution.

A significant advantage of the lyophilization procedure of the present invention is that it provides for an extended shelf life as compared to that of the class of ocyalkylamides or even their vitamin complexes in solution. For example, the shelf life of a solution of the ascorbic acid complex of N-cyclohexyl-N-methyl-4-(2-oxo-1,2,3,5-tetrahydro-imidazo-[2,1-b]quinazolin-7-yl)oxybutyramide is only about 5 days. The lyophilized product prepared according to the formulation method of the present invention can be expected to permit a shelf life of at least two years.

The reason for the generally brief shelf lives in solution is that the class of oxyalkylamides has limited solution-phase stability. For example, kinetic studies of N-cyclohexyl-N-methyl-4-(2-oxo-1,2,3,5-tetrahydroimidazo-[2,1-b]quinazolin-7-yl)oxybutyramide have demonstrated that its degradation is both acid and base catalyzed, and that in solution, it has an estimation shelf life of only six months at about pH 6, and pH of maximum stability. At pH 2, at which the compound is formulated, shelf life ($T_{90}$) is less than a week. In a concentrated form in neat dimethylacetamide, polyethylene glycol or the like, the $T_{90}$ is only about three weeks.

Accordingly, in order to maximize the stability of such a compound for parenteral administration therapy, the present inventors have developed a lyophilization procedure. The lyophilization substantially removes water: the primary nucleophile responsible for the degradative hydrolysis of the compound in solution. When the vitamin/compound complex is lyophilized, the product will have a substantially superior shelf life over any solution phase formulation of the compound yet developed. Stability data for the lyophilized powder at accelerated temperature and under various states of humidity are set forth in the following table (Table 1). The data in this table indicate that the formulation has good chemical and physical stability.

TABLE 1

Solid State Stability of
N—cyclohexyl-N—methyl-4-(2-oxo-1,2,3,5-tetrahydro-imidazo-[2,1-b]quinazolin-7-yl)oxybutyramide
in Lyophilized Powders[a]

| Temp. °C. | Storage[b] Condition | Results[c] Appearance (Color) | % Remaining | | |
|---|---|---|---|---|---|
| | | | 5 days | 7 days | 36 days |
| 5 | Capped | White | — | 99.2 | — |
| 25 | Capped | White | — | 100 | 99.7 |
| 25 | 47% RH capped | White | — | 100 | 100 |
| RT | 47% RH holes | White | — | 100 | 100 |
| 40 | Capped | Light yellow | — | 100 | 94.4 |
| 40 | 47% RH capped | Light yellow | — | 100 | 96.7 |
| 40 | 47% RH capped | Light yellow | 99.2 | 99.2 | 94.5 |

[a] Made from 2 mL of t-BuOH/AA/H$_2$O (50/10/40) with pH = 2.0 and 6.5 mg N—cyclohexyl-N—methyl-4-(2-oxo-1,2,3,5-tetrahydroimidazo-2,1-b]-quinazolin-7-yl)oxybutyramide 130 mL
[b] Capped means: not stored in the desiccator with the vial sealed. 47% RH capped and 47% RH holes mean: stored in a 47% relatively humidity desiccator with the vial capped or covered with aluminum foil with 4 holes in the foil respectively.
[c] After 7 days.

The lyophilization procedure is preferably carried out in a lower chain alcohol, more preferably in ethanol, isopropanol, tert-butyl alcohol or n-propanol, and most preferably in ethanol, which further enhances the solubility of the complex.

UTILITY

The utility of the present invention lies in the formulation of cardiotonic PDE inhibitors (preferably the compounds of the generic formula I), such that the compounds can be effectively administered to a person or mammal in need thereof.

The compounds of the generic formula I (as defined in the Summary of the Invention) are potent inhibitors of human platelet 3',5'-cyclic AMP phosphodiesterase activity. As a consequence, these compounds inhibit the ADP-induced aggregation of human platelets. Thus, these compounds are useful in the prevention or treatment of a variety of conditions related to platelet aggregation and thrombosis, such as, intravascular thrombosis, prevention of coronary thrombosis, prevention of transient ischemic episodes and prevention of platelet thrombosis and the prevention of thrombosis, thrombocytopenia or platelet activation associated with the use of prosthetic devices (artificial heart valves, etc.).

3',5'-cyclic AMP is known to regulate the activity of numerous enzymes and to mediate the action of several hormones. Studies have demonstrated that a deficiency in this cyclic AMP or an increase in the activity of a high affinity 3',5'-cyclic AMP phosphodiesterase is associated with a variety of disease states. As inhibitors of 3',5'-cyclic AMP phosphodiesterase, compounds of this type are useful in the treatment or prevention of hypertension, asthma, diabetes, obesity, immune dysfunctions, psoriasis, inflammation, cardiovascular disease, tumor metastasis, cancer and hyperthyroidism.

The compounds of the generic formula I also have inotropic activity. They can strengthen myocardial contraction force by which the heart ventricles can pump the blood into the periphery. Consequently, these compounds also are useful in treating myocardial failure.

DEFINITIONS

The compounds of Formula I that are formulated in accordance with the present invention are numbered as follows:

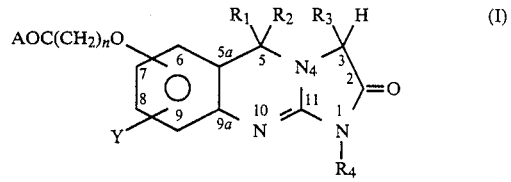

For the purpose of this disclosure, these compounds are represented as having the single structural formulation represented by Formula I. However, when R$_4$ is hydrogen, compounds of Formula I can exist in several possible tautomeric forms established by the following core structures:

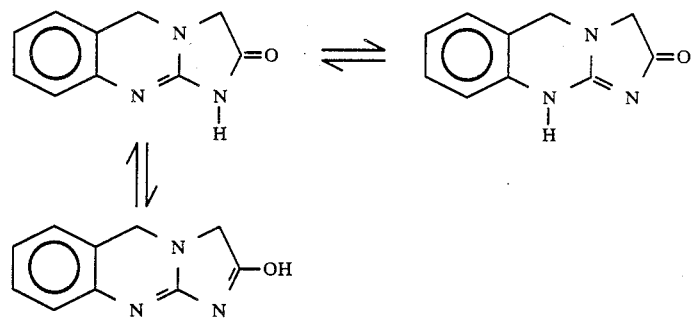

All tautomers are to be considered as within the scope of the compounds represented by Formula I.

The compounds formulated in accordance with this invention may be prepared as structural isomers wherein the oxyalkylamide side chain is substituted on the benzene ring at any of the four different available positions. This fact is graphically represented in the generic formula by the drawing of the line into the benzene ring without it being directed to a particular carbon. In addition, the Y substituent or substituents may be present at any of one or more of the remaining ring positions as indicated by Formula I.

Also within the scope of the compounds represented by Formula I are the optical isomers of those compounds having an asymmetric center, such as when positions 3 and/or 5 of the 1,2,3,5-tetrahydroimidazo[2,1-b]quinazolin-2-one structure are substituted with a substituent other than hydrogen. In addition, $R_5$ may have an asymmetric center.

Accordingly, the compounds may be prepared either in optically active form or as racemic mixtures. The scope of the subject invention herein is not limited to formulations including the racemic mixture, but also encompasses formulations of the separated individual optical isomers of the compounds of Formula (I).

If desired, the compounds to be formulated may be resolved into their optical antipodes by conventional resolution means, for example, by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-α-sulfonic acid, camphoric acid, menthoxyacetic acid, tartaric acid, malic acid, diacetyltartarkic acid, pyrrolidine-5-carboxylic acid and the like. The separated pure diastereomeric salts may then be cleaved by standard means to afford the respective optical isomers.

For the purposes of this invention, the following phrases should be understood to have the recited meaning.

The term "water-soluble vitamin" refers to any vitamin having a water solubility in excess of 200 mg/ml in pure water, such as thiamine, nicotinamide, pyridoxine, and ascorbic acid, or any pharmaceutically acceptable salt of the foregoing. The term "vitamin" is to be construed as a cofactor needed for enzyme function and/or activity and capable of charge donation and/or acceptance.

When reference is made to "alkyl of 1 to 6 carbon atoms" it is meant that there is a branched or unbranched saturated hydrocarbon chain containing, in total, that number of carbon atoms. The phrase refers specifically to such substituents as, for example, methyl, ethyl, n-propyl, i-propyl, n-butyl, tert-butyl, n-pentyl, n-hexyl and the like. The terms "alkyl of 1 to 4 carbon atoms" and "lower alkyl" are used interchangeably and mean methyl, ethyl, n-propyl, i-propyl, n-butyl, t-butyl and the like. The term "alkyl" or the prefix "alk" (as in "alkoxy"), when not inconsistently qualified (e.g., by the term "lower"), means a branched or unbranched saturated hydrocarbon chain containing from 1 to 12 carbon atoms.

"Lower alkoxy" means the group —OR wherein R is lower alkyl as defined in the foregoing paragraph.

The group "lower chain alcohol" means the group —ROH wherein R is lower alkyl as defined above, preferably alkyl of 1 to 4 carbons.

When it is recited that $R_1$ and $R_2$ can be combined to form an oxo group, it is meant that at position 5, as numbered above, the carbon has a double bond to an oxygen atom.

An "hydroxyalkyl" substituent is comprised of 1 to 6 carbon atoms, carbon, hydrogen and one oxygen atom, i.e. an alcohol wherein one terminal carbon atom is substituted on the amide nitrogen and the hydroxyl group is substituted on another carbon, preferably the ω-carbon. Herein the alkyl chain may be straight or branched, preferably straight, is fully saturated and, except for the hydroxyl group, has no other substitution. Examples of hydroxyalkyl substituents are 2-hydroxyethyl, 3-hydroxypropyl, 4-hydroxybutyl, 5-hydroxypentyl and 6-hydroxyhexyl. This is not an exhaustive list of hydroxyalkyl substituents which can be prepared or which can be used in this invention. It is merely intended to exemplify and identify that which is being referred to by the aforementioned phrase.

In the instance where the $R_3$ group and/or the nitrogen in the amide-forming group is substituted with a hydroxyalkyl substituent, that hydroxy function can be converted to an ester by reaction with a carboxylic acid. Such an acid may be any unbranched or branched aliphatic acid having 1 to 6 carbon atoms such as, for example, formic acid, acetic acid, propionic acid, butyric acid, pentanoic acid, hexanoic acid or an isomer of these acids which has up to 6 carbon atoms and is fully saturated. These esters are referred to herein as "aliphatic acylates of 1 to 6 carbon atoms." In addition, the carboxylic acid may be an aryl acid, exemplified by benzoic acid and having up to 7 to 12 carbon atoms. Representative radicals are, in addition to benzoic acid, phenylacetic acid, 3-phenylpropionic acid, 4-phenylbutyric acid, 6-phenylhexanoic acid and the like. Such acids serve to define and exemplify the term directed to the ester product of the reaction, "aryl acylates of 7 to 12 carbon atoms."

The term, "α-amino acid side chains," is meant to include amino acid side chains on naturally occurring amino acids and on commercially available synthetic amino acids, as well as amino acid side chains which can be synthesized by one of ordinary skill in the art of organic chemistry; where in each instance the amine group and the side chain are both attached to the α-carbon. Examples include amino acid side chains such as those found on cysteine, tyrosine, histidine, arginine, proline, phenylalanine, methionine, etc.

The phrase "unsubstituted or substituted" is used herein in conjunction with cycloalkyl and aryl substituents to indicate the ring may have on it only hydrogen or, alternatively, may be substituted with one or more of the enumerated radicals as specifically indicated.

"Cycloalkyl of 3 to 8 carbon atoms" refers to a saturated aliphatic ring which contains 3 to 8 carbon atoms and which is substituted directly onto the nitrogen without any intervening methylene groups. Such radicals are, for example, cyclopropyl, cyclobutyl, cyclopentyl, cyclohexyl, cycloheptyl and cyclooctyl.

When reference is made to "cycloalkyl lower alkyl of 4 to 12 carbon atoms," it is meant that the substituents denoted as cycloalkyl of 3 to 8 carbon atoms in the preceding paragraph are attached to the nitrogen (to which $R_5$ is attached) by means of a saturated branched or unbranched carbon chain which may have 1 to 4 carbon atoms. Such substituents are, for example, cyclobutylmethyl, 4-cyclobutylbutyl, cyclopentylmethyl, 4-cyclopentylbutyl, cyclohexylmethyl, 4-cyclohexylbutyl, cycloheptylmethyl and 4-cycloheptylbutyl.

In addition, the cycloalkyl or cycloalkyl lower alkyl radicals recited in the two foregoing paragraphs may be substituted on the ring with a radical chosen from the group consisting of lower alkyl, lower alkoxy, —OH, —OCOR$_7$, halo, —NH$_2$, —N(R$_7$)$_2$, —NHCOR$_7$, —COOH, and —COO(R$_7$) wherein R$_7$ is lower alkyl.

"Phenyl lower alkyl" means a group having at least one and up to four methylene groups with an ω-phenyl group. In this instance the carbon chain is linear, not branched. The phenyl group may be unsubstituted, i.e., contain only hydrogen, or it may be substituted with up to 5 substituents of a single functionality or a combination of the several recited substituents. Examples of unsubstituted phenyl lower alkyl are benzyl, phenylethyl, phenylpropyl and phenylbutyl. Examples of substituted phenyl lower alkyl are 4-halophenylalkyl, 2,4-dihalophenylalkyl, 2,4,6-trihalophenylalkyl or 2,3,4,5,6-pentahalo-phenylalkyl wherein halo is as defined below. In addition, the phenyl group may be substituted with one or more lower alkyl groups such as methyl, ethyl, propyl, or the like. One or more lower alkoxy groups may also be substituted on the phenyl ring. Also, phenyl may be substituted with a radical chosen from the group consisting of $-NH_2$, $-N(R_7)_2$, $-NHCOR_7$, $-COOH$, and $-COOR_7$ group wherein $R_7$ is lower alkyl.

The term "halo" refers to fluoro, chloro, bromo and iodo.

The prefixes D- and L- are used to describe the individual optical isomers having an asymmetric center at the 3 or 5 position in the 1,2,3,5-tetrahydroimidazo[2,1-b]guinazolin-2-one structure.

Perhexylenyl refers to the substituent dicyclohexyl-2-(2-piperidyl)ethane which is disclosed in British Pat. No. 1,025,578.

"Pharmaceutically acceptable salt" refers to those salts which retain the biological properties and efficacy of the free acid or base and which are not biologically or otherwise undesirable, formed with inorganic or organic acids or bases. Inorganic acids which may be used are, for example, hydrochloric acid, hydrobromic acid, sulfuric acid, nitric acid, phosphoric acid and the like. Exemplary organic acids are acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid at the like.

The compounds of Formula I in free base form may be converted to the acid addition salts by treating the base with a stoichiometric excess of the appropriate organic or inorganic acid. Typically, the free base is dissolved in a polar organic solvent such as ethanol or methanol, and the acid added thereto. The temperature is maintained between about 0° C. and about 100° C. The resulting acid addition salt precipitates spontaneously or may be brought out of solution with a less polar solvent.

An "aqueous/organic solvent system" refers to an aqueous or aqueous/cosolvent mixture, where the co-solvent is a lower chain alcohol.

When reference is made to "the drug" in describing the preferred formulations of the present invention, it is intended to refer to the class of compounds which are cardiotonic PDE inhibitors, particularly compounds of Formula I as defined above, unless otherwise specified. Weight measurements of the drug are in free-base equivalents unless otherwise specified or apparent from the context.

When reference is made to a "formulation" of the present invention, it should be understood that in the broadest sense the term refers to the lyophilized product of the combination of the drug and the vitamin. However, it should be understood that other excipients can also be present in the formulations, as will be noted below.

ADMINISTRATION AND DOSAGE

Administration of the formulations of the compounds of Formula (I) and salts thereof can be via any of the accepted modes of administration for agents which are cyclic AMP phosphodiesterase inhibitors. These methods include oral, nasal, ophthalmic, topical, parenteral and otherwise systemic or aerosol forms.

Depending on the intended mode of administration, the formulations used may be in the form of solid, semi-solid or liquid dosage forms, such as, for example, ointments, creams, tablets, suppositories, pills, capsules, powders, liquids, suspensions, or the like, preferably in unit dosage forms suitable for single administration of precise dosages. The formulations may include a conventional pharmaceutical carrier or excipient as well as the compound of Formula (I) and the water-soluble vitamin (or the pharmaceutically acceptable salts of the compound and/or the vitamin), and in addition, may include other medicinal agents, pharmaceutical agents, carriers, adjuvants, etc.

For oral administration, a pharmaceutically acceptable non-toxic formulation can be formed by the incorporation of any of the normally employed excipients, such as, for example, pharmaceutical grades of mannitol, lactose, starch, magnesium stearate, sodium saccharin, talcum, cellulose, glucose, sucrose, magnesium, carbonate, and the like. Such formulations take the form of solutions, suspensions, tablets, pills, capsules, powders, sustained release formulations and the like. Such formulations may contain from about 1% to about 99%, and preferably about 10% to about 50%, of a cardiotonic PDE inhibitor, such as a compound of Formula (I) or a pharmaceutically acceptable salt thereof.

Parenteral administration is generally characterized by injection, either subcutaneously, intramuscularly or intravenously. This is the preferred administration route. Injectables can be prepared in conventional forms, either as liquid solutions or suspensions, solid forms suitable for solution or suspension in liquid prior to injection, or as emulsions. Suitable excipients are, for example, water, saline, mannitol, dextrose, glycerol, ethanol or the like. In addition, if desired, the formulations to be administered may also contain minor amounts of non-toxic auxiliary substances such as wetting or emulsifying agents, pH buffering agents and the like, such as for example, sodium acetate, sorbitan monolaurate, triethanolamine oleate, etc. It is preferred to maintain the formulations at a pH of about 2.

For systemic administration via suppository, traditional binders and carriers include, e.g. polyalkylene glycols or triglycerides. Such suppositories may be formed from mixtures containing active ingredient in the range of from about 0.5% to about 40%.

The amount of active compound administered will of course, be dependent on the subject being treated, the type and severity of the affliction, the manner of administration and the judgment of the prescribing physician. In any case, a therapeutically effective amount of the drug either alone or in combination with the various excipients listed above or otherwise known will be administered. For the purposes of this invention, a therapeutically effective amount to be administered as a total dosage is in the range of from about 10 μg of the drug (measured as free base) per kg of body weight to about 100 μg/kg. In the context of parenteral administration, a therapeutically effective concentration would be in the range of from about 0.1 to about 50 mg/ml.

Different specifically preferred dosage ranges (as measured in free base equivalents of the drug) are considered for toxicological studies and for recommended clinical dosages. For human clinical dosages, from about 10 to about 100 μg of the drug per kg of body weight would be considered a broad dosage range. More preferably, the dosage would not be greater than about 30 μg/kg, and most preferably, the dosage would be kept to a level below about 20 μg/kg. When considering the doses that would be administered to mammals in toxicological studies as wellas those that would be administered clinically, the broadest recommended dosage range would be from about 0.01 mg/kg to about 15 mg/kg; the more preferred range would be from about 0.01 mg/kg to about 5 mg/kg; and the most preferred range would be from about 0.01 mg/kg to about 1 mg/kg. The drugs can be administered orally or parenterally, and in the latter case, by bolus or by infusion over 24 hours.

THE PREFERRED FORMULATIONS AND PREPARATIONS

Generally, the formulations of this invention are prepared by complexing a compound of Formula (I) with a water-soluble vitamin. This is accomplished by contacting a compound of Formula (I) with a water-soluble vitamin under conditions which allow the formation of the complex, and then lyophilizing the reslting product.

Important parameters in addressing the preferred formulations and preparations are: (1) the specifically preferred compounds of Formula (I) and the relative concentrations thereof; (2) the preferred vitamins and the relative concentrations thereof; (3) the solvent system and the conditions (time, temperature and pH) for preparing the formulation to be lyophilized; and (4) the lyophilization procedure.

Preferred embodiments of the present invention are those compounds of Formula (I) wherein n is 3 or 4; $R_1$, $R_2$ and $R_3$ are hydrogen and $R_4$ is hydrogen or methyl, or compounds wherein n is 3 or 4, $R_1$, $R_2$ and $R_4$ are hydrogen, $R_3$ is alkyl of 1 to 6 carbon atoms, phenyl, benzyl, hydroxy lower alkyl and its acylates or carbamoyl alkyl and their optical isomers.

More preferred embodiments are those compounds wherein n is 3 or 4; $R_1$, $R_2$ and $R_3$ are hydrogen; $R_4$ is hydrogen or methyl; and A is an amide wherein the nitrogen is substituted with alkyl of 1 to 6 carbon atoms, hydroxyalkyl of 1 to 6 carbon atoms and its aliphatic acylates of 1 to 6 carbon atoms or aryl acylates of 7 to 12 carbon atoms, cycloalkyl of 3 to 8 carbon atoms, cycloalkyl lower alkyl of 4 to 12 carbon atoms, phenyl or phenyl lower alkyl unsubstituted or substituted with 1 or more lower alkyl, halo or lower alkoxy groups; perhexylenyl; (±)-decahydroquinolinyl; morpholinyl; piperidinyhl; pyrrolindinyl; tetrahydroquinolinyl; tetrahydroisoquinolinyl or indolinyl, or compounds wherein n is 3 or 4, $R_1$, $R_2$ and $R_4$ are hydrogen, $R_3$ is alkyl of 1 to 6 carbon atoms, phenyl, benzyl, hydroxy lower alkyl and its acylates or carbamoyl alkyl and A is an amide wherein the nitrogen is substituted with alkyl of 1 to 6 carbon atoms or cycloalkyl of 3 to 8 carbon atoms and their optical isomers.

In the most preferred embodiments, the compound of Formula (I) is N-cyclohexyl-N-methyl-4-(2-oxo-1,2,3,5-tetrahydroimidazo-[2,1-b]quinzaolin-7-yl)oxybutyramide or a pharmaceutically acceptable salt thereof.

Most preferably, the hydrogen sulfate salt having the structure:

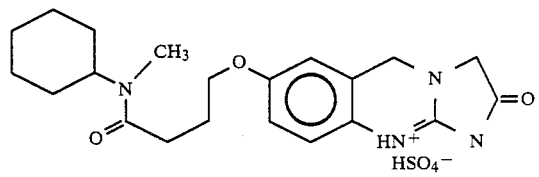

is used in the formulation.

Other preferred compounds include: anagrelide, cilostimide, sulmazole (ARL,115), amrinone, milrinone, rolipram (2K-62,711), fenoximone (MDL-17,043) CI-930, CI-914, MY-5445, piroximone (MDL-19,205) and M&B-22,948.

Additionally, in most preferred embodiments of the invention, the water-soluble vitamin is selected from the group consisting of ascorbic acid, nicotinamide, thiamine and pyridoxine. It is preferred that a molar excess of the water-soluble vitamin be used to obtain favorable equilibrium conditions for the formation of the complex. For example, when ascorbic acid is used as a complexing agent, an amount of N-cyclohexyl-N-methyl-4-(2-oxo-1,2,3,5-tetrahydroimidazo-[2,1-b]quinazolin-7-yl)oxybutyramide ("the above-named drug") in the range of fromabout 0.1 to about 10 mg/ml (where the drug weight is measured as free-base equivalent) and an amount of vitamin in the range of from about 10 mg/ml to about 300 mg/ml can be used in the formulation. More preferred is to supply the above-named the drug in a concentration of from about 0.1 to about 5 mg/ml, and to supply ascorbic acid in the range of from about 50 to about 100 mg/ml. In the most preferred embodiment, 1 to 5 mg/ml of the above-named drug will be used, mixed with 100 mg/ml of ascorbic acid.

Alternatively, if either pyridoxine, nicotinamide or thiamine is used in the formulation, the above-named drug will be supplied in the range of from about 0.1 to about 1 mg/ml and the vitamin will be supplied in the range of from about 1 to about 300 mg/ml. More preferably, the above-named drug will be supplied in the range of from about 0.5 to about 1 mg/ml, and the vitamin will be supplied in the range of from about 30 to about 50 mg/ml. Most preferably, the above-named drug will be supplied at a concentration of about 1 mg/ml, with 50 mg/ml of pyridoxine, nicotinamide or thiamine.

Figure 3:
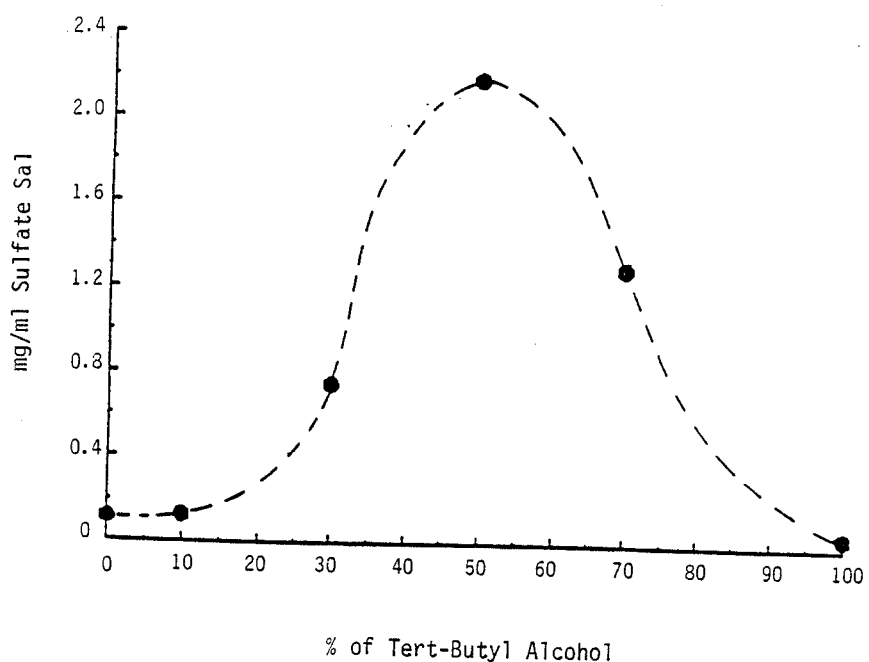
FIG. 3 is a graph showing solubility characteristics of N-cyclohexyl-N-methyl-N-methyl-4-(2-oxo-1,2,3,5-tetrahydroimidazo-[2,1-b]quinazolin-7-yl)oxybutyramide in water and tert-butyl alcohol.

In one of the preferred preparations, tert-butyl alcohol is used as a co-solvent in which the drug and the vitamin are dissolved prior to lyophilization. In combination with a water-soluble vitamin, such as ascorbic acid, this alcohol is instrumental in initially getting all the drug into solution (see FIG. 3). From about 10 to about 90% (v/v) of tert-butyl alcohol can be used, although, more preferably, from about 10 to about 50% (v/v) is used, and most preferably, from about 30 to about 50% (v/v) of tert-butyl alcohol is used. Ultimately, essentially all the tert-butyl alcohol will be removed by sublimation during the lyophilization process. The residual tert-butyl alcohol in the final product could be, for example, in the range of from about 0 to about 5% (w/w).

When ethanol is used as the cosolvent in which the drug and the vitamin are dissolved prior to lyophilization, from about 10 to 50% (v/v) of ethanol is used, preferably from about 10–20% (v/v).

In the most preferred embodiments, the solution before lyophilization is at a pH of about 2 and comprises the sulfate salt of N-cyclohexyl-N-methyl-4-(2-oxo-1,2,3,5-tetrahydroimidazole-[2,1-b]quinazolin-7-yl)oxybutyramide; a water-soluble vitamin selected from the group consisting of ascorbic acid, pyridoxine, thiamine and nicotinamide; tert-butyl alcohol; and sufficient sulfuric acid to adjust the pH of the solution to about 2.0. In one embodiment, mannitol can also be added to the solution. Although up to 200 mg/ml of mannitol can be used in the preferred embodiments, it is more preferred to keep the concentration of mannitol to about 100 mg/ml, and most preferred to use from about 10 to about 50 mg/ml. Details of suitable quantities that can be used in specifically preferred embodiments are given in the examples.

It is preferred that the solution containing the drug and the vitamin be prepared at a temperature of between about 20° and about 30° C., and most preferred that the temperature be about 25° C. The solution is preferably stirred until essentially all of the drug is dissolved, typically for at least about 15 to about 20 minutes.

According to the present invention, the solution is then lyophilized. Lyophilization dramatically increases the water solubility of the drug, and additionally enhances stability. The combination of the lyophilization technique with the use of complexing agents such as ascorbic acid, pyridoxine, nicotinamide and thiamine results in an easy-to-handle, stable product having very high water solubility. The lyophilized powder may later be reconstituted for use in parenteral or oral administration.

In general, the solution is prepared for lyophilization by filtering the solution to sterilize it, using, for example, a cellulose filter. During the lyophilization process the aqueous/organic solvent, such as water and the lower alcohol cosolvent are removed by sublimation. The preferred lyophilizaton cycle is set forth in Example I. The dried lyophilization powder comprises the drug, a water-soluble vitamin such as ascorbic acid, and optionally, mannitol. There could also be residual water (0.1–10% w/w), as well as residual tert-butyl alcohol, as noted above. The lyophilized powder can be reconstituted with any parenterally or orally acceptable solvent. The powder is easily handled and reconstitutes quickly, as noted in the examples.

PREPARATION AND EXAMPLES

The drugs themselves are prepared in accordance with U.S. Pat. Nos. 4,490,371 and 4,551,459. Accordingly, the "Preparations and Examples" of U.S. Pat. No. 4,490,371, U.S. patent application Ser. No. 599,858, and U.S. patent application Ser. No. 744,100, are specifically incorporated by reference at this point of the present disclosure.

The following examples describe in detail the formulations according to the most preferred embodiments of the present invention.

EXAMPLE 1

Complexation of N-cyclohexyl-N-methyl-4-(2-oxo-1,2,3,5-tetrahydroimidazo-[2,1-b]quinazolin-7-yl)oxybutyramide with ascorbic acid 6.5 grams of the sulfate salt of N-cyclohexyl-N-methyl-4-(2-oxo-1,2,3,5-tetrahydroimidazo[2,1-b]quinazolin-7-yl)oxyburyamide were dissolved, along with 100 grams of ascorbic acid, 500 ml of tert-butyl alcohol, sufficient sulfuric acid to adjust the pH to 2.0, and sufficient water to bring the volume to 1 liter. The solution was stirred at room temperature for about 10 minutes and filtered with a 0.22 micron Milipore TM cellulose filter. 5 Milliliters of the solution were then dispensed into a 10 ml vial for lyophilization. In the lyophilization procedure, the condenser temperature was initially set to give a shelf temperature of $-60°$ C., and the pressure was initially atmospheric. After the product had frozen, the pressure was gradually dropped to 10 milliTorr, and the vacuum was held for about a day. Still under vacuum, the shelf temperature was slowly raised by incrementally increasing the temperature to the following values for about 6 hours at each value: $-40°$ C., $-20°$ C.; $-10°$ C.; 0° C.; and 15°–25° C. During this lyophilization process, all the butanol and water were removed. The final lyophilized powder comprised 32.5 milligrams of N-cyclohexyl-N-methyl-4-(2-oxo-1,2,3,5-tetrahydroimidazo-[2,1-b]quinazolin-7-yl)oxybutyramide sulfate salt and 500 milligrams of ascorbic acid, some residual water (4% w/w) and tert-butyl alcohol (3% w/w) per vial.

EXAMPLE 2

Complexation of N-cyclohexyl-N-methyl-4-(2-oxo-1,2,3,5-tetrahydroimidazo-[2,1-b]quinazolin-7-yl)oxybutyramide with ascorbic acid and mannitol Following the same procedure as outlined above, the drug has also been formulated with 50 grams of ascorbic acid, 20 grams of mannitol and 6.5 grams of sulfate salt of the title compound. The end lyophilized product in each vial comprised 32.5 milligrams of the sulfate salt of N-cyclohexyl-N-methyl-4-(2-oxo-1,2,3,5-tetrahydroimidazo-[2,1-b]quinazolin-7-yl)oxybutyramide (equivalent to 5 mg of free base), 250 milligrams of ascorbic acid and 100 milligrams of mannitol.

EXAMPLE 3

Complexation of N-cyclohexyl-N-methyl-4-(2-oxo-1,2,3,5-tetrahydroimidazo-[2,1-b]quinazolin-7-yl)oxybutyramide with pyridoxine and mannitol Following the same procedure, 50 grams of pyridoxine hydrochloride were substituted for the 50 grams of ascorbic acid in Example 2. In this instance, only 1.3 grams of N-cyclohexyl-N-methyl-4-(2-oxo-1,2,3,5-tetrahydroimidazo-[2,1-b]quinazolin-7-yl)oxybutyramide sulfate salt were used. The final lyophilization powder comprised 6.5 milligrams of N-cyclohexyl-N-methyl-4-(2-oxo-1,2,3,5-tetrahydroimidazo-[2,1-b]quinazolin-7-yl)oxybutyramide sulfate salt and 250 milligrams of pyridoxine HCl.

EXAMPLE 4

Complexation of N-cyclohexyl-N-methyl-4-(2-oxo-1,2,3,5-tetrahydroimidazo-[2,1-b]quinazolin-7-yl)oxybutyramide with nicotinamide and mannitol Complexation with nicotinamide is accomplished by using the same weight-volume proportions as discussed in Example 3.

EXAMPLE 5

Complexation of N-cyclohexyl-N-methyl-4-(2-oxo-1,2,3,5-tetrahydroimidazo-[2,1-b]quinazolin-7-yl)oxybutyramide with ascorbic acid Following the same procedure as outlined in Example 1, but using ethanol as the co-solvent, 0.456 grams of the sulfate salt of the title compound were dissolved along with 20 grams of ascorbic acid, 200 ml of ethanol, sufficient sulfuric acid to adjust the pH to 2.0, and sufficient water to bring the volume to 1 liter.

EXAMPLE 6

Preparation of Injectable or Intravenous Solution

The drug is initially dissolved in sterile water: 5 mg (measured as free base equivalents of the compound of Examples 1–4) per ml of water. The solution is then diluted 1:10 (vol/vol) with isotonic saline. 3 ml of this dilution can be delivered as a bolus injection for acute therapy, resulting in a 20–30 μg/kg dose. Alternatively, a 300 μg/kg infusion can be given over 24 hours (i.e., a total volume of between about 280 ml and about 300 ml can be adminstered in this manner).

We claim:

1. A lyophilized complex of:
   a water-soluble vitamin selected from the group consisting of ascorbic acid, pyridoxine, thiamine, nicotinamide, or a pharmaceutically acceptable salt thereof; and
   a cardiotonic phosphodiesterase inhibitor of the formula

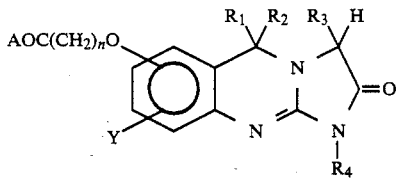

an optical isomer thereof, or a pharmaceutically acceptable salt thereof wherein:
n is an integer of 1 to 6;
$R_1$ is hydrogen or alkyl of 1 to 4 carbons;
$R_2$ is hydrogen or $R_1$ and $R_2$ are combined to form an oxo group;
$R_3$ is hydrogen, alkyl of 1 to 6 carbons, phenyl, benzyl, hydroxy lower alkyl or an aliphatic acylate thereof of 1 to 6 carbon atoms or an aryl acylate thereof of 7 to 12 carbon atoms, carbamoyl alkyl, carboxyalkyl, alkoxycarbonylalkyl or an α-amino acid side chain;
$R_4$ is hydrogen, alkyl of 1 to 6 carbons, benzyl, or hydroxy lower alkyl;
Y is hydrogen, alkyl of 1 to 4 carbon atoms, halo or lower alkoxy;

A is $NR_5R_6$ wherein $R_5$ and $R_6$ are independently selected from the group consisting of: hydrogen; alkyl of 1 to 6 carbon atoms; hydroxyalkyl of 1 to 6 carbon atoms or an aliphatic acylate thereof of 1 to 6 carbon atoms or an aryl acylate thereof of 7 to 12 carbon atoms; cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_7$, halo, —NH$_2$, —N(R$_7$)$_2$, —NHCOR$_7$, —COOH, or —COO(R$_7$) group wherein $R_7$ is lower alkyl; phenyl or phenyl lower alkyl wherein phenyl is unsubstituted or substituted with at least one lower alkyl, halo or lower alkoxy group or an —NH$_2$, —N(R$_7$)$_2$, —NHCOR$_7$, —COOH, or —COOR$_7$ group wherein $R_7$ is lower alkyl; or wherein $R_5$ and $R_6$ are combined to form a compound selected from the group consisting of: morpholinyl; piperidinyl; perhexylenyl; N-loweralkylpiperazinyl; pyrolidinyl; tetrahydroquinolinyl; tetrahydroisoquinolinyl; (±)-decahydroquinolinyl and indolinyl.

2. The complex of claim 1 wherein the compound of Formula (I) is N-cyclohexyl-N-methyl-4-(2-oxo-1,2,3,5-tetrahydroimidazo-[2,1-b]quinazolin-7-yl)-oxybutyramide, or a pharmaceutically acceptable salt thereof.

3. The complex of claim 2 wherein the compound of Formula (I) is the sulfate salt of N-cyclohexyl-N-methyl-4-(2-oxo-1,2,3,5-tetrahydroimidazo-[2,1-b]quinazolin-7-yl)oxybutyramide.

4. The complex of claim 1 wherein the vitamin is ascorbic acid or pyridoxine, or a pharmaceutically acceptable salt of any of the foregoing.

5. The complex of claim 2 wherein the vitamin is ascorbic acid or pyridoxine, or a pharmaceutically acceptable salt of any of the foregoing.

6. The complex of claim 1 wherein the vitamin or salt thereof is present in a molar excess of the compound of Formula I.

7. The complex of claim 5 wherein the vitamin or salt thereof is present in a molar excess of the compound of Formula I.

8. A lyophilized complex of:
   the sulfate salt of N-cyclohexyl-N-methyl-4-(2-oxo-1,2,3,5-tetrahydroimidazo-[2,1-b]quinazolin-7-yl)oxybutyramide; and
   ascorbic acid present in a molar excess of the sulfate salt.

9. An injectable formulation comprising the complex of claim 1.

10. An injectable formulation comprising the complex of claim 2.

11. An injectable formulation comprising the complex of claim 3.

12. An injectable formulation comprising the complex of claim 4.

13. An injectable formulation comprising the complex of claim 5.

14. An injectable formulation comprising the complex of claim 6.

15. An injectable formulation comprising the complex of claim 7.

16. An injectable formulation comprising the complex of claim 8.

17. The formulation of claim 9, wherein the complex is made up into an aqueous solution.

18. The formulation of claim 10, wherein the complex is made up into an aqueous solution.

19. The formulation of claim 11, wherein the complex is made up into an aqueous solution.

20. The formulation of claim 12, wherein the complex is made up into an aqueous solution.

21. The formulation of claim 13, wherein the complex is made up into an aqueous solution.

22. The formulation of claim 14, wherein the complex is made up into an aqueous solution.

23. The formulation of claim 15, wherein the complex is made up into an aqueous solution.

24. The formulation of claim 16, wherein the complex is made up into an aqueous solution.

* * * * *